United States Patent [19]

Mock

[11] 4,254,283

[45] Mar. 3, 1981

[54] PROCESS FOR PREPARING ADIPIC ACID WITH RECOVERY OF GLUTARIC AND SUCCINIC ACIDS

[75] Inventor: George H. Mock, Pensacola, Fla.

[73] Assignee: Monsanto Company, St. Louis, Mo.

[21] Appl. No.: 46,274

[22] Filed: Jun. 7, 1979

[51] Int. Cl.³ .................. C07C 51/31; C07C 51/43; C07C 51/44; C07C 55/14

[52] U.S. Cl. .................. 562/530; 260/346.74; 260/346.76; 562/513; 562/593

[58] Field of Search ............ 562/528, 593, 530, 513; 260/346.76, 346.74

[56] References Cited

U.S. PATENT DOCUMENTS

| | | | |
|---|---|---|---|
| 3,096,369 | 7/1963 | Soeterbroek et al. | 562/593 |
| 3,359,283 | 12/1967 | Campbell et al. | 562/593 |

FOREIGN PATENT DOCUMENTS 1470169  4/1977  United Kingdom ............ 562/593

*Primary Examiner*—Vivian Garner
*Attorney, Agent, or Firm*—Thomas Y. Awalt, Jr.

[57] ABSTRACT

In the manufacture of adipic acid by nitric acid oxidation of cyclohexanol and cyclohexanone glutaric and succinic acids are recovered from the reaction by-product and waste stream by crystallizing adipic acid and succinic acid out of the stream leaving glutaric acid in the residue; forming succinic anhydride from the succinic acids so obtained; separating the succinic anhydride from the adipic acid by distillation thereby to recover succinic acid in anhydride form; and crystallizing, thereby to recover, the glutaric acid from the residue.

7 Claims, 2 Drawing Figures

PROCESS FOR PREPARING ADIPIC ACID WITH RECOVERY OF GLUTARIC AND SUCCINIC ACIDS

BACKGROUND OF THE INVENTION

A. Field of the Invention

This invention relates to a method for the reclamation of organic dibasic acids from certain process streams. More particularly, it relates to a method of producing succinic anhydride and glutaric acid crystals and separating these materials from a mixture of dibasic acids including succinic acid, glutaric acid and adipic acid. Such a mixture of acids is contained in the reaction by-product and waste stream after nitric acid oxidation of cyclohexane and cyclohexanol and removal of most of the product adipic acid.

B. The Prior Art

A well-known commercial method of producing adipic acid involves a series of steps including: (1) the oxidation of cyclohexane in a liquid phase with air or other molecular oxygen-containing gas to a mixture of cyclohexanol and cyclohexanone at rather low conversion but with high yields; (2) the separation of the unoxidized cyclohexane from the mixed cyclohexanol and cyclohexanone intermediate reaction product; (3) the final oxidation of the intermediate product with a strong oxidizing acid, such as nitric acid, to adipic acid and minor amounts of other dibasic organic acids, including glutaric acid and succinic acid; and (4) the isolation of the adipic acid from these by-product organic acids, such as by crystallization. Mother liquor from the first or crude crystallization is further treated by means known to the art to recover nitric acid, adipic acid, and the oxidation catalyst. It is concentrated to recover nitric acid, cooled to recover adipic acid, and passed over an ion exchange resin for catalyst recovery. The remaining mother liquor is handled by the waste disposal system.

This reaction by-product and waste stream or "mother liquid", in addition to the aforesaid organic dibasic acids, may contain relatively minor amounts of miscellaneous organic acids, as well as nitric acid and water. A typical adipic plant stream may run as high as thirty thousand pounds per hour, with the following representative composition:

|  | Percent by weight |
|---|---|
| H$_2$O | 78.0 |
| HNO$_3$ | 1.9 |
| Miscellaneous organic acids | 1.0 |
| Adipic acid (HOAd) | 2.7 |
| Succinic acid (HOSu) | 4.2 |
| Glutaric acid (HOGl) | 12.2 |

Because of the difficulty in, and the poor economics of, further treatment, the mother liquor is commonly disposed of by deep well methods, or by concentration and incineration. This represents not only a substantial loss of valuable chemicals, the most important of which are the by-product dibasic acids, but also creates environmental problems.

It has been proposed heretofore to treat a mixture of dibasic acids of the homologous series indicated above to obtain succinic anhydride from such a mixture. In the known procedure the mixture after removal of the free water was heated in the presence of certain water-entraining agents at a temperature in the range of 175°–220° C. Succinic acid in the mixture was dehydrated to the anhydride form selectively from all the other dibasic acids present therein. The water of dehydration and its entraining agent were evaporated from the resulting mixture to the exclusion of succinic anhydride. In accordance with this known method, the separation of the succinic anhydride from the other components in the evaporation residue was rendered more facile by the lixiviation thereof with liquid sulfur dioxide. While such procedure may effect a separation of the succinic values in the mixture, there were several drawbacks. In the first place, the employment of an extraneous chemical was required, thereby increasing the cost and complexity of the process. In addition, glutaric acid still remained associated with adipic acid; and it was believed that these two acids could not be separated one from the other conveniently.

It has also been proposed to remove the water and nitric acid, then form the anhydride of both succinic and glutaric acids, separating and recovering each successively by distillation. Since some product degradation inevitably accompanies the anhydride-forming process because of the elevated temperature requirements any process or step of a process which can avoid such formation is to be desired.

Contrary to popular belief, glutaric and adipic acid can be separated one from the other conveniently and economically, thus providing a recovery route which eliminates the necessity of forming an anhydride from the glutaric acids and thereby alleviating the cost of making the glutaric anhydride and of separating the glutaric anhydride from succinic anhydride.

SUMMARY OF THE INVENTION

According to the present invention, after substantially all of the nitric acid is removed by evaporation from the nitric acid mother liquor, adipic and succinic acids are crystallized from the aqueous residue, leaving glutaric acid in the residue. The crystallization of adipic and succinic acids can be conducted in two stages, e.g., successively at temperatures of about 45° C.–55° C. and 20° C.–30° C. Succinic anhydride is then formed from the succinic acid obtained by the crystallization. This succinic anhydride is separated from the adipic acid (and any other matter remaining after the crystallization step) by distillation. The glutaric acid, which was left in the aqueous residue, is crystallized and thereby recovered directly from it. The crystallization of glutaric acid can be conducted in two stages, e.g., at 10°–20° C. and 20°–30° C.

In the detailed description of the preferred embodiment, reference will be made to the Drawing in which:

FIG. 1 is a graph showing relative solubilities of glutaric, adipic and succinic acids under various temperature conditions; and FIG. 2 is a flow sheet showing the process of this invention.

DESCRIPTION OF THE PREFERRED EMBODIMENTS

As stated above, the mother liquor from the manufacture of adipic acid ordinarily comprises a nitric acid solution containing succinic acid, glutaric acid, and adipic acid. As used herein the term "mother liquor" is applied to the stream after removal of the adipic acid by a crystallization step. Although some adipic acid remains in the mother liquor at this point, further crystallization of adipic acid by an additional crystal cropping operation would result in the simultaneous crystallization of succinic acid.

In order to recover the oxidation catalyst in the ion exchange system it is essential that the mother liquor be rendered substantially free of nitric acid before being processed in accordance with this invention. Removal of nitric acid can be effected as described in U.S. Pat. No. 3,359,283, by evaporation under suitable pressure and temperature conditions at which the nitric acid is evaporated from the mother liquor. Preferably, the mother liquor is passed continuously through an evaporator of conventional construction maintained at a temperature sufficiently high to induce evaporation of substantially all the acid and water and to keep the inspissated organic dibasic acid material as a molten residue. A temperature of about 120° C. and a reduced pressure of 80 mm of mercury are quite suitable conditions to effect efficient evaporation. However, these conditions can be varied widely. A suitable process for stripping nitric acid with steam is described in U.S. Pat. No. 4,014,903.

Figure 2:
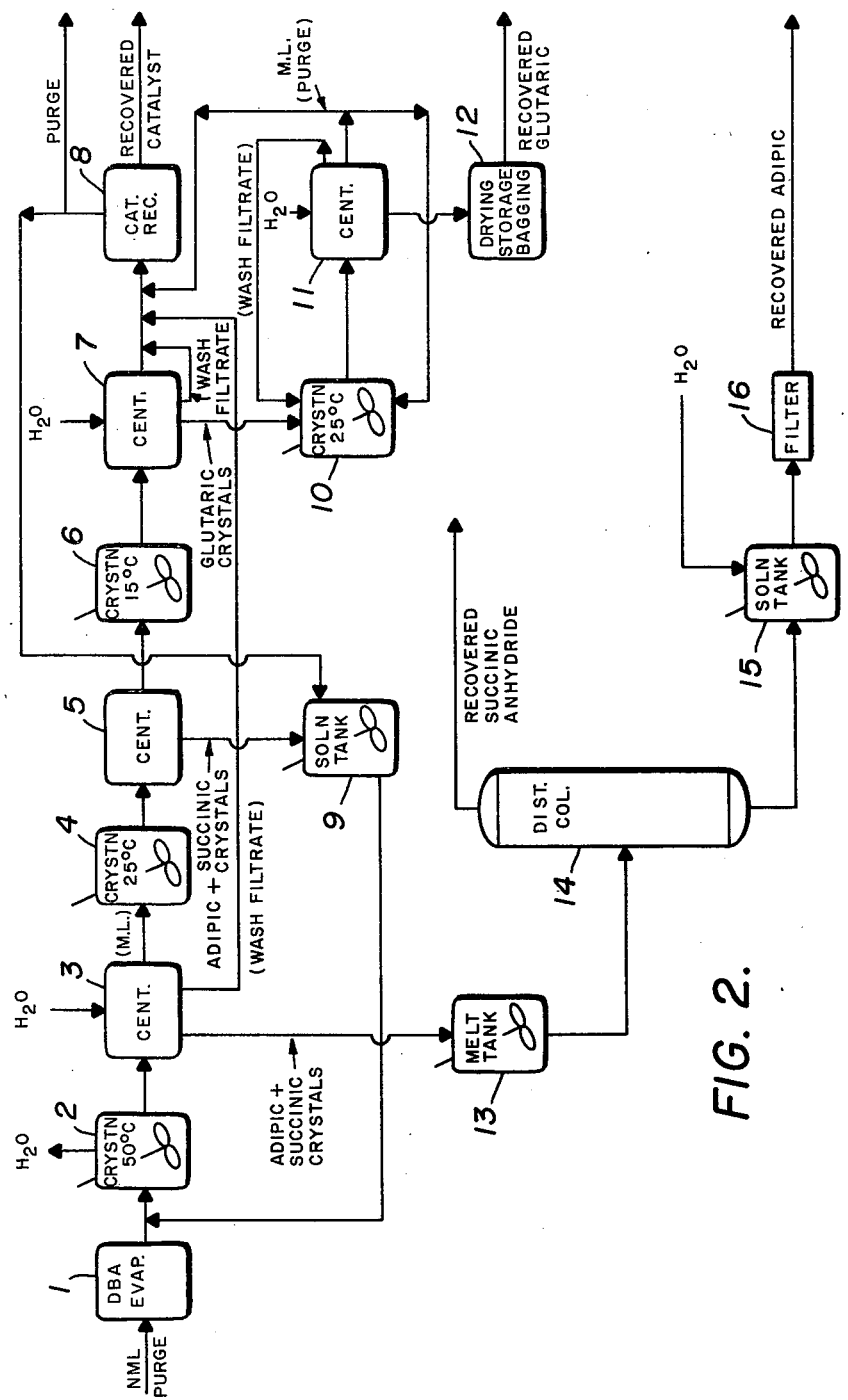

In order to obtain a more complete understanding of the present invention, reference is now made to the accompanying drawing in which FIG. 2 is a block flow diagram illustrating a continuous process system, a preferred embodiment of this invention. Adipic mother liquor containing nitric acid is supplied to dibasic acid evaporator 1 where the dibasic acid concentration of the mother liquor is adjusted to about 85%, by removing water and nitric acid present. The evaporation residue of evaporator 1 is then piped to crystallization vessel 2 in which a first cropping of adipic acid succinic crystals is made at about 50° C. The crystals are then transferred to centrifuge 3 for separation from the evaporation/crystallization residue. These crystals (of the order of about 150–500 microns) are transferred to melt container 13 and melted for subsequent separation by distillation. The mother liquor residue from centrifuge 3 is transferred to crystallization vessel 4 where at 25° C. a second phase of crystallization takes place whereupon smaller crystals (1–100 microns in size) are formed and transferred to centrifuge 5 whereupon the additional adipic and succinic crystals are separated and dissolved in solution container 9 for subsequent recycling to the first phase of crystallization in vessel 2. The remaining evaporation/crystallization residue (mother liquor) is transferred to crystallization vessel 6 wherein, at about 15° C., glutaric acid is crystallized therefrom and transferred to centrifuge 7 for removal. The glutaric crystals removed by centrifuge 7 are transferred to a second phase crystallization vessel 10 where they are remelted and recrystallized at 25° C., and transferred to centrifuge 11 for separation and subsequent drying, storing and bagging at location 12. The remaining evaporation/crystallization residue (mother liquor) from centrifuge 7, along with the wash filtrate from centrifuge 3 and another from centrifuge 11 is transferred to catalyst recovery vessel 8 where catalyst is recovered by methods well known in the art.

From vessel 13, the melted adipic and succinic crystals are transferred to distillation column 14, where, in accordance with technology well known in the art, and as explained in U.S. Pat. No. 3,359,283 (hereby incorporated by reference), and in accordance with melting points and boiling points shown in column 5 thereof, succinic anhydride is distilled from the top of the column, and adipic acid is removed from the bottom, dissolved in solution tank 15, filtered in filter 16, and thereafter recovered.

Figure 1:
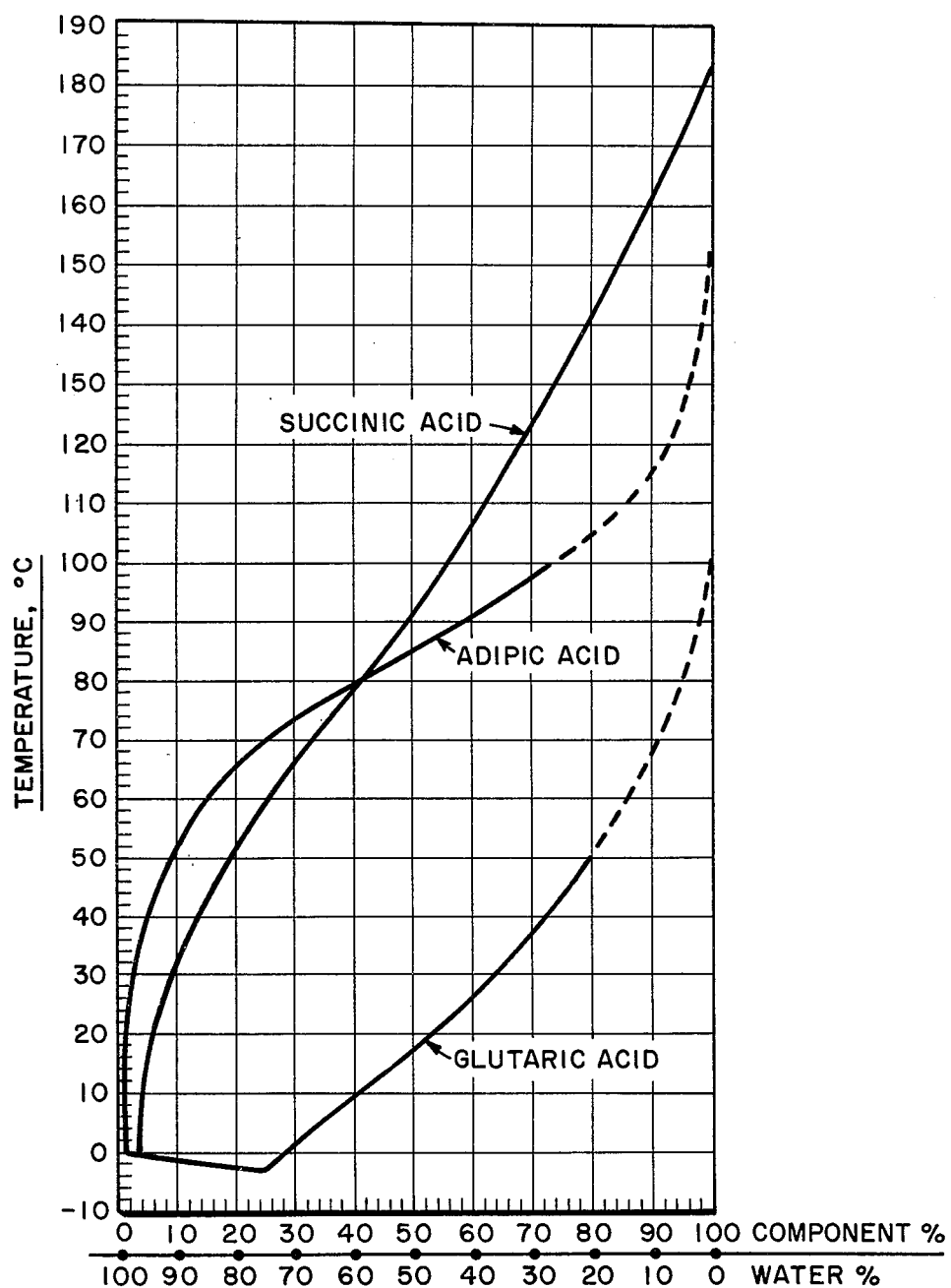

As indicated above, glutaric acid can be easily separated by crystallization because of the high solubility of glutaric as opposed to the low solubility of adipic and succinic acid in water, as shown at FIG. 1. By diluting the evaporation residue with water and cooling to about 25° C., most of the adipic and succinic can be crystallized, the glutaric remaining dissolved in the mother liquid. By filtering and washing the crystals, a reasonably pure mixture of adipic and succinic can be obtained. Since the mother liquor is nearly saturated with glutaric, it can be cooled to produce a sizeable amount of crude glutaric crystals. Although some adipic and succinic is included in these crystals, the amounts are insignificant. High purity glutaric is produced by recrystallization in aqueous solutions.

Various modifications of the invention will be apparent to those skilled in the art. Hence, it will be understood that the invention is not limited to the foregoing description or annexed drawing except as defined in the appended claims.

I claim:

1. In a process for the production of adipic acid by nitric acid oxidation of cyclohexanol and cyclohexanone, where the product adipic acid is recovered from an aqueous mother liquor containing nitric acid, succinic acid, glutaric acid and adipic acid, and where substantially all of the nitric acid is subsequently removed by evaporation, and where succinic acid and glutaric acid are thereafter recovered from the nitric acid evaporation residue, the process improvement comprising:
   (1) crystallizing adipic acid and succinic acid from the nitric acid evaporation residue, leaving glutaric acid;
   (2) forming succinic anhydride from the succinic acid obtained by the crystallization (1);
   (3) separating the succinic anhydride from the adipic acid by distillation;
   (4) crystallizing and thereby recovering the glutaric acid left from (1).

2. The process of claim 1 wherein the crystallization of adipic and succinic acids is conducted in two stages.

3. The process of claim 2 wherein the crystallization of adipic and succinic acids is conducted successively at temperatures of about 45° C.–55° C. and 20° C.–30° C.

4. The process of claim 2 wherein the crystallization of adipic and succinic acids is conducted successively at temperatures of about 50° C. and 25° C.

5. The process of claim 1 wherein the crystallization of glutaric acid is conducted in two stages.

6. The process of claim 5 wherein the crystallization of glutaric acid is conducted at 10°–20° C. and 20°–30° C.

7. The process of claim 5 wherein the crystallization of glutaric acid is conducted at 15° C. and 25° C.

* * * * *